United States Patent
Smolko-Schvarzmayr et al.

(10) Patent No.: US 10,543,493 B2
(45) Date of Patent: Jan. 28, 2020

(54) SYNTHESIS OF NEW ANIONIC SURFACTANTS AND THEIR USE AS COLLECTORS IN FROTH FLOTATION OF NON-SULPHIDIC ORES

(71) Applicant: NOURYON CHEMICALS INTERNATIONAL B.V., Arnhem (NL)

(72) Inventors: Natalija Smolko-Schvarzmayr, Hjälteby (SE); Anders Klingberg, Henån (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 1041 days.

(21) Appl. No.: 14/899,220

(22) PCT Filed: Jul. 2, 2014

(86) PCT No.: PCT/EP2014/064014
§ 371 (c)(1),
(2) Date: Dec. 17, 2015

(87) PCT Pub. No.: WO2015/000931
PCT Pub. Date: Jan. 8, 2015

(65) Prior Publication Data
US 2016/0129456 A1    May 12, 2016

(30) Foreign Application Priority Data

Jul. 5, 2013 (EP) .................................... 13175270

(51) Int. Cl.
B03D 1/016   (2006.01)
B03D 1/02    (2006.01)
(Continued)

(52) U.S. Cl.
CPC ............ B03D 1/016 (2013.01); B03D 1/021 (2013.01); C07C 237/12 (2013.01);
(Continued)

(58) Field of Classification Search
CPC .. H04B 7/2615; H04L 5/0007; H04W 72/042; H04W 72/044; H04W 76/27;
(Continued)

(56) References Cited

U.S. PATENT DOCUMENTS

| | | |
|---|---|---|
| 1,453,695 A | 5/1923 | O'Connor |
| 2,744,825 A | 5/1956 | Thompson et al. |

(Continued)

FOREIGN PATENT DOCUMENTS

| | | |
|---|---|---|
| DE | 1162305 | 7/1959 |
| DE | 257398 A1 | 6/1988 |

(Continued)

OTHER PUBLICATIONS

Bunting et al., "The Hydrolysis of Esters of N-Hippurylglycine and N-Pivaloyl Glycine by Carboxypeptidase A," Biochimica et Biophysica Acta, 524, 1978, p. 393-402.

(Continued)

*Primary Examiner* — Latosha Hines
(74) *Attorney, Agent, or Firm* — Lorenz & Kopf, LLP

(57) ABSTRACT

The present invention relates to a compound obtainable by reacting an N-acyl neutral amino acid or a salt thereof, or an N-acyl neutral amino acid oligopeptide or a salt thereof with a monohydroxy monocarboxylic acid or a salt thereof. This compound is useful as a collector in a process for froth flotation of non-sulfidic ores, especially phosphate ores. The invention also relates to a method which comprises the steps of a) conditioning a pulped phosphate ore, wherein the phosphate ore comprises a calcium phosphate mineral or a mixture of such minerals, and gangue minerals, with an effective amount of a calcium phosphate mineral collector reagent, which is the above-mentioned compound, and optionally other flotation aids and b) performing a froth flotation process to recover the calcium phosphate mineral(s).

14 Claims, 1 Drawing Sheet

A graphic representation of the values in Table 2.

(51) Int. Cl.
   *C08G 69/44* (2006.01)
   *C08G 63/685* (2006.01)
   *C08G 69/10* (2006.01)
   *C07C 237/12* (2006.01)
   *C08G 69/36* (2006.01)

(52) U.S. Cl.
   CPC ......... *C08G 63/6852* (2013.01); *C08G 69/10* (2013.01); *C08G 69/36* (2013.01); *C08G 69/44* (2013.01); *B03D 2201/02* (2013.01); *B03D 2203/04* (2013.01); *B03D 2203/06* (2013.01)

(58) Field of Classification Search
   CPC ....... H04W 88/02; B03D 1/016; B03D 1/021; B03D 2201/02; B03D 2203/04; B03D 2203/06; C07C 237/12; C08G 63/6852; C08G 69/10; C08G 69/36; C08G 69/44
   See application file for complete search history.

(56) References Cited

U.S. PATENT DOCUMENTS

| | | | |
|---|---|---|---|
| 3,074,980 A | | 1/1963 | Lorentzen |
| 3,425,549 A | * | 2/1969 | Dickson ............... B03D 1/016 209/166 |
| 3,985,722 A | | 10/1976 | Yoshida et al. |
| 4,457,850 A | | 7/1984 | Tesmann et al. |
| 4,720,339 A | * | 1/1988 | Nagaraj ............... B03D 1/016 209/167 |
| 4,732,667 A | | 3/1988 | Hellsten et al. |

FOREIGN PATENT DOCUMENTS

| | | |
|---|---|---|
| DE | 4105384 A1 | 8/1991 |
| EP | 0201815 A2 | 11/1986 |
| EP | 0649836 A1 | 4/1995 |
| EP | 0857717 A1 | 8/1998 |
| EP | 1672055 A1 | 6/2006 |
| GB | 1197672 | 7/1970 |
| RU | 1453695 C * | 11/1994 |
| WO | 91/15298 A1 | 10/1991 |
| WO | 91/18674 A1 | 12/1991 |
| WO | 92/21443 A1 | 12/1992 |
| WO | 93/06935 A1 | 4/1993 |
| WO | 98/08597 A1 | 3/1998 |
| WO | 2004/007417 A1 | 1/2004 |
| WO | 2008/019807 A1 | 2/2008 |
| WO | 2009/065530 A2 | 5/2009 |
| WO | 2009/087086 A1 | 7/2009 |
| WO | 2013/010650 A1 | 1/2013 |
| WO | 2013/014268 A1 | 1/2013 |
| WO | 2013/047458 A1 | 4/2013 |

OTHER PUBLICATIONS

Ping et al., "Reaction Versus Subsite Stereospecificity of Peptidylglycine α-Monooxygenase and Peptidylamidoglycolate Lyase, the Two Enzymes Involved in Peptide Amidation," The Journal of Biological Chemistry, vol. 270, No. 49, 1995, p. 29250-29255.

Bugg et al., "Molecular Basis for Vancomycin Resistance in *Enterococcus faecium* BM4147: Biosynthesis of a Depsipeptide Peptidoglycan Precursor by Vancomycin Resistance Proteins VanH and VanA," Biochemistry, 1991, 30, p. 10408-10415.

Lee et al., "First Principles Investigation of Vancomycin and Teicoplanin Binding to Bacterial Cell Wall Termini," Journal of the American Chemical Society, 126, p. 8384-8385, 2004.

European Patent Application for EP 13175270.1, dated Apr. 14, 2014.

J.S. Hanson et al., Interaction of Glycine and a Glycine-Based Polymer with Xanthate in Relation to the Flotation of Sulfide Minerals, International Journal of Mineral Processing, 23 (1988), pp. 123-135.

M. Martins et al., Surface Tension of Flotation Solution and Its Influence on the Selectivity of the Separation Between Apatite and Gangue Minerals, Minerals & Metallurgical Processing, vol. 26, No. 2, May 2009, pp. 79-84.

* cited by examiner

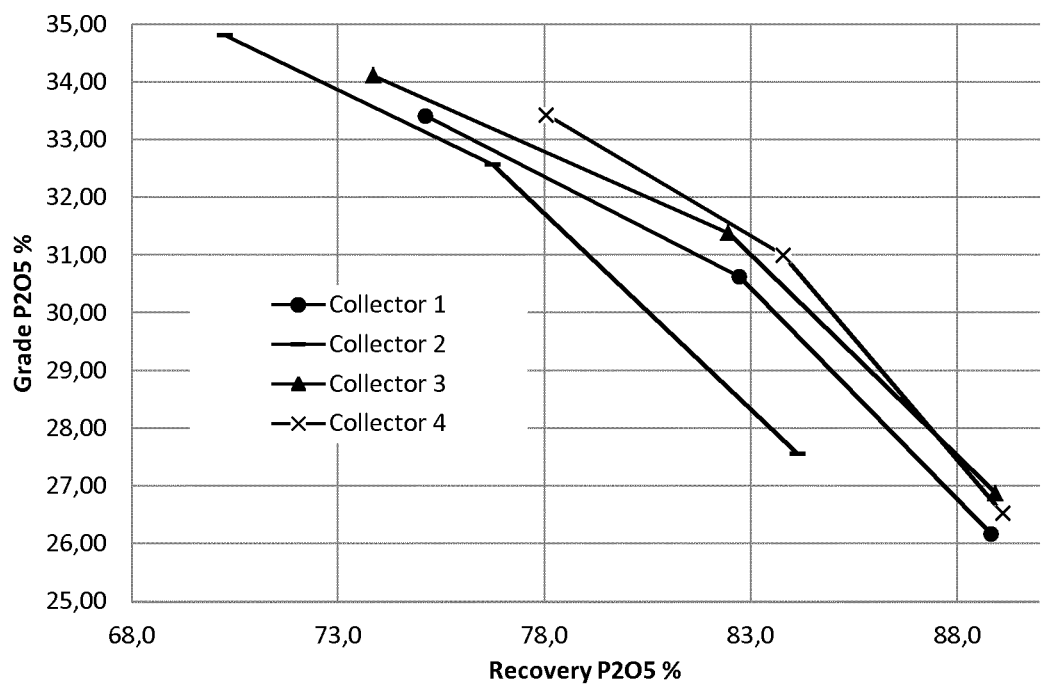
A graphic representation of the values in Table 2.

SYNTHESIS OF NEW ANIONIC SURFACTANTS AND THEIR USE AS COLLECTORS IN FROTH FLOTATION OF NON-SULPHIDIC ORES

This application is a national stage filing under 35 U.S.C. § 371 of PCT/EP2014/064014, filed Jul. 2, 2014, which claims priority to European Patent Application No. 13175270.1, filed Jul. 5, 2013, the contents of which are each incorporated herein by reference in their entireties.

TECHNICAL FIELD OF INVENTION

The present invention relates to novel fatty acid derivatives and the use of these derivatives as collectors for the froth flotation of non-sulphidic ores, especially phosphate ores.

TECHNICAL BACKGROUND OF THE INVENTION

Phosphate rocks contain calcium phosphate minerals largely in the form of apatite, usually together with other minerals, e.g. silicate minerals and carbonate minerals, such as calcite. Apatite is a generic name for a group of calcium phosphate minerals also containing other elements or radicals, such as fluorapatite, chlorapatite, hydroxylapatite, carbonate-rich fluorapatite and carbonate-rich hydroxylapatite.

Phosphate ore froth flotation is a conventional process for recovering apatite from ore pulps. Most widely used anionic flotation agents for flotation of phosphate ores are the unsaturated fatty acids, for example oleic acid, and the technical grades or commercial grades of naturally-occurring fatty acid mixtures having a high proportion of unsaturated fatty acids, such as tall oil, acids from soybean oil, cottonseed oil and linseed oil, and derivatives thereof, as well as synthetic acids. The unsaturated fatty acid flotation agents are known to be comparatively non-selective because they are also suitable for the flotation of carbonate containing minerals, and therefore have only limited use in cases where accompanying minerals such as these have to be separated off from the valuable apatite minerals. There are a lot of suitable anionic surfactants proposed to be used as flotation agents for calcium phosphate, such as, for example, alkyl benzene sulfonates, alkyl phosphates, alkyl sulfates, alkyl sulfosuccinamates, alkyl sulfosuccinates, alkyl lactylates and alkyl hydroxamates. It is also known that these types of surfactants usually cannot be used in a pure form since they do not provide right froth characteristics during the flotation process, and therefore anionic surfactants are usually used in formulations together with other anionic (especially of fatty acid type) or nonionic surfactants.

However there is a need for new formulations of collectors for complex, for example weathered, ores, which are selective, based on renewable raw materials and easily manufactured.

WO 93/06935 discloses a method for producing iron-ore concentrates by the flotation washing (reverse flotation) of iron ore using as the collector mixtures containing at least one ether amine, and at least one other anionic and/or nonionic collector, which may be e.g. an acyl lactylate or a sarcoside. WO 92/21443 discloses a collector mixture for the flotation of non-sulfidic ores, which contains salts of sulfonation products of unsaturated fatty acids and salts of sulfonation products of unsaturated fatty acid glycerine esters, plus, optionally other anionic and/or nonionic surface-active agents, which may be acyl lactylates or sarcosides. WO 91/18674 discloses dicarboxylic acid esters with fatty acid monoalkanolamides as collectors for the flotation of non-pyritiferous ores, in particular apatite, and these collectors may also be mixed with acyl lactylates or sarcosides, and WO 91/15298 discloses the same collector for the flotation of non-sulfidic ores. U.S. Pat. No. 4,457,850 discloses acyl lactylates as flotation aids for the flotation of non-sulfidic minerals, WO 98/08597 discloses an emulsifier blend containing an acyl lactylate as the primary emulsifier and a nonionic surfactant as the coemulsifier, and U.S. Pat. No. 2,744,825 discloses the preparation of acyl lactylates. U.S. Pat. No. 4,732,667 discloses a process for froth flotation of iron ores, containing silicate and phosphate minerals that are floated away from the iron, using a collector mixture of a primary amine and e.g. a sarcoside. EP 0 201 815 B1 discloses the use of mixtures of at least one EO/PO adduct of a fatty alcohol and at least one anionic, cationic or ampholytic surfactant, that may be e.g. an acyl lactylate or a sarcoside, as collectors in the flotation of non-sulfidic ores.

However, there is still a need for more efficient collectors to be used in the froth flotation of phosphate ores to recover apatite.

SUMMARY OF THE INVENTION

It is an object of the present invention to provide a collector for use in a method for froth flotation of non-sulfide ores, especially phosphate ores, wherein said collector is very efficient in recovering apatite in the presence of silicate and/or carbonate minerals.

Now it has surprisingly been found that a collector, which is an anionic surfactant being an ester between a monohydroxy monocarboxylic acid and an N-acyl neutral amino acid or a salt thereof, or an N-acyl neutral amino acid oligopeptide or a salt thereof, preferably a lactic acid ester and/or polylactic acid ester of an N-acyl neutral amino acid, is significantly improving the recovery of apatite from phosphate ores.

DETAILED DESCRIPTION OF THE INVENTION

A first aspect of the present invention relates to a compound which is an ester between a monohydroxy monocarboxylic acid and an N-acyl neutral amino acid, or an N-acyl neutral amino acid oligopeptide.

A second aspect relates to a composition comprising the above-mentioned compound, an N-acyl neutral amino acid or a salt thereof and a fatty acid or a salt thereof.

A third aspect of the invention is the use of said compound or composition as a collector reagent in a method for froth flotation of non-sulfidic ores, especially phosphate ores.

The ester between a monohydroxy monocarboxylic acid and an N-acyl neutral amino acid or an N-acyl neutral acid oligopeptide is obtainable by reacting an N-acyl neutral amino acid or a salt thereof, or an N-acyl neutral amino acid oligopeptide or a salt thereof with a monohydroxy monocarboxylic acid or a salt thereof.

The compound is preferably described by the formula

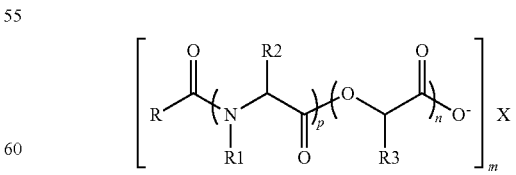

where R is a hydrocarbyl group having from 7 to 23, preferably 11 to 21, carbon atoms, optionally substituted; $R_1$ is H or $CH_3$, preferably H; $R_2$ is H or a C1-C4 alkyl group, preferably H; $R_3$ is H or $CH_3$, preferably $CH_3$; n is a number 1-20; p is a number 1-3, preferably 1; X is $H^+$ or a cation which is organic or inorganic, and m represents the valency of the cation and is a number 1-2, preferably 1. The cation is preferably selected from the group consisting of an alkali metal cation, an alkaline earth metal cation, ammonium, and a substituted ammonium group having one or more $C_1$ to $C_3$ alkyl and/or hydroxyalkyl groups.

The first step to make the product of formula (I) is to synthesize an N-acyl neutral amino acid. By a neutral amino acid is meant an amino acid that has an equal number of amino and carboxylic acid groups. The synthesis of an N-acyl neutral amino acid is well known in literature and commonly involves a condensation reaction of an acyl halide, usually acyl chloride, and a neutral amino acid, e.g. sarcosine or glycine, in the presence of alkali. The salt which is formed during the reaction has to be removed by filtration after the reaction is completed. This kind of procedure has been the subject of a number of patent publications, see e.g. GB 1,197,672, EP 0 857 717 B1, WO 2009/065530, and WO 2013/010650. Also a number of other methods to produce the N-acyl amino acid have been published. EP 0 649 836 B1 discloses a process using an amidonitrile as an intermediate, which is hydrolysed to the acylamino acid. U.S. Pat. No. 3,074,980 discloses a process using higher molecular weight fatty acid anhydrides in a reaction with lower molecular weight aliphatic α-amino monocarboxylic acid salts. U.S. Pat. No. 3,985,722 relates to a process where a mixed acid anhydride consisting of higher fatty acid and sulphuric acid is used as an acylating agent in the reaction with amino acids. RU 2083558 teaches the preparation of N-acyl-amino acids or their salts by adding aqueous alkaline metal salts obtained from lower aliphatic amino acids or protein hydrolysates to an appropriate fatty acid ester at 140-160° C., and WO 2013/014268 discloses a similar method. EP 1 672 055 discloses a method of preparation where a neutral amino acid, a long chain fatty acid and an alkaline substance are mixed and the mixture is heated while water is removed. WO 2008/019807 describes a process for preparing acylglycinate from a fatty acid monoethanolamide which is oxidized with oxygen in the presence of a transition group metal catalyst in an alkaline medium to give an acylglycinate salt, and WO 2009/087086 describes a similar method.

The N-acyl group of the N-acyl neutral amino acid is a group R—(C=O)—, where R is a hydrocarbyl group having from 7 to 23 carbon atoms, which is optionally substituted. The hydrocarbyl group may be linear or branched, saturated or unsaturated. When substituted, the substituents are normally one or more hydroxyl groups. The fatty acid to use for the synthesis of the N-acyl neutral amino acid may suitably be tall oil fatty acid, coco fatty acid, tallow fatty acid, soya fatty acid, rape seed fatty acid, myristoleic acid, palmitoleic acid, oleic acid, linoleic acid, α-linolenic acid, arachidonic acid, erucic acid, myristic acid, palmitic acid, stearic acid, arachidic acid, behenic acid, and mixtures thereof. An example of a fatty acid that is substituted is ricinoleic acid, which is substituted by a hydroxyl group in the 12 position. The most preferred fatty acids are unsaturated.

Suitable neutral amino acids are glycine, alanine, sarcosine, valine, leucine and isoleucine, preferably glycine.

When producing the N-acyl neutral amino acid, there could be a further polymerisation of additional amino acids to produce an N-acyl neutral amino acid oligopeptide, but preferably only one mole of amino acid is added per mole of the fatty acid derivative, and the main product will mainly contain only one amino acid unit.

In the next step to obtain the compound of the present invention, the monohydroxy monocarboxylic acid is added to the alkali salt of the N-acyl neutral amino acid to produce an ester of the N-acyl neutral amino acid. Suitable monohydroxy monocarboxylic acids are lactic acid and glycolic acid, preferably lactic acid.

It has further been found that it is beneficial to use as a collector a composition comprising
a) the compound as described above, b) an N-acyl neutral amino acid or a salt thereof, and c) a fatty acid RCOOH, where R is a hydrocarbyl group having from 7 to 23 carbon atoms, optionally substituted, or a salt thereof.

Suitably, a) is present in an amount of 1-20 mol %, b) is present in an amount of 30-60 mol % and c) is present in an amount of 40-60 mol %, wherein the amounts are calculated based on the total molar amount of a), b) and c).

In another aspect, the invention relates to a method for froth flotation of non-sulfidic ores, especially phosphate ores, for the recovery of apatite minerals, in which method the compound or composition described above is used as a collector.

Such froth flotation method for phosphate ores may typically comprise the steps:
a) conditioning a pulped phosphate ore, wherein the ore comprises a calcium phosphate mineral or a mixture of such minerals, and gangue minerals, with an effective amount of a calcium phosphate mineral collector reagent, which is a compound or composition as defined herein, and optionally other flotation aids and
b) performing a froth flotation process to recover the calcium phosphate mineral(s).

Optionally, the pulped ore may be conditioned with an effective amount of a depressant prior to adding the mineral collector.

By using the collector defined herein in the froth flotation of a phosphate ore, it is possible to achieve a better recovery of calcium phosphate while keeping the grade of the product at the same level, as compared to using the corresponding N-acyl amino acid on its own.

The effective amount of the collector of the present invention will depend on the amount of impurities present in the pulped apatite ore and on the desired separation effect, but will in general be in the range of from 10 to 1000 g/ton dry ore, preferably in the range of from 20 to 500, more preferably from 100 to 400 g/ton dry ore.

In yet another aspect, the present invention relates to a pulp comprising crushed and ground phosphate ore, a calcium phosphate mineral collector reagent as defined herein, and optionally a depressant and further flotation aids.

Suitable depressants may be e.g. a polysaccharide, alkalized starch, or dextrin.

Further flotation aids that may be present in the froth flotation method are extender oils, and frothers/froth regulators, such as pine oil, MIBC (methylisobutyl carbinol) and alcohols such as hexanol and alcohol ethoxylates/propoxylates.

The present invention is further illustrated by the following examples.

EXAMPLES

Example 1

Synthesis of Lactic Acid Ester of N-Acyl Glycine 84.66 g (0.3056 mol) of tall oil fatty acid, 11.2 g (0.1493 mol) of glycine and 8.39 g (0.1495 mol) of KOH dissolved in 30 ml of ethanol were added to a round bottom flask, which was fitted with a condenser, a thermometer, a heating mantle, a nitrogen inlet and a mechanical stirrer. The reaction mixture was heated up to 80° C. and the ethanol was distilled off. After the removal of the ethanol the temperature of the reaction mixture was raised to 153-156° C., and the pressure was stepwise decreased to 13 mbar. The progress of the reaction was followed by $^1$H-NMR spectroscopy. After 2 h at 155° C. and 13-50 mbar there was no unreacted glycine remaining. Then the reaction temperature was decreased to 110° C., and 0.1493 mol of lactic acid as an 80% water solution was added. The reaction mixture was heated 1.5 h at 100-120° C. and atmospheric pressure, and then 1 h at 120-150° C. and a pressure of 13 mbar. The final product was analysed by $^1$H-NMR spectroscopy. $^1$H-NMR (CDCl$_3$): δ 0.9 (—(CH$_2$)$_n$—CH$_3$); δ 1.3 (—CH$_2$—CH=CH—CH$_2$—CH=CH—CH$_2$—(CH$_2$)$_n$—CH$_3$); δ 1.6 (—NH—CO—CH$_2$—CH$_2$—); δ 2.1 (—CH$_2$—CH=CH—CH$_2$—CH=CH-CH$_2$—(CH$_2$)$_n$—CH$_3$); δ 2.2-2.3 (—NH—CO—CH$_2$—CH$_2$—); δ 2.8 (—CH$_2$—CH=CH-CH$_2$—CH=CH—CH$_2$—(CH$_2$)$_n$—CH$_3$); δ 3.6-3.9 (COOH-CH$_2$—NH—CO—CH$_2$—); 3.9-4.1 (COOH—CH(CH$_3$)—COO—CH$_2$—NH—CO—CH$_2$—); δ 5.4 (—CH$_2$—CH=CH—CH$_2$—CH=CH—CH$_2$—(CH$_2$)$_n$—CH$_3$); δ 7.4 (—NH—CO—). By the use of $^1$H, $^{13}$C and 2D NMR techniques the amounts of the components of the obtained composition of the final product were estimated. The degree of polymerization of lactic acid ester of N-acyl glycine was calculated from the following formula:

$$n = \frac{\text{mol of added lactic acid to the reaction mixture}}{\text{integral at } \delta(3,9 - 4,1)/2}$$

For the product lactic acid ester of N-acyl glycine in Collector 4 the average degree of polymerization was estimated to be around 8.

Example 2

Flotation Experiments

General Flotation Procedure

The phosphate ore containing 25-30% of apatite, 24-28% of silicates and about 20% of iron oxides was crushed and ground to a desirable flotation size (K80=180 μm). 500 g of the ore was placed into a 1.4 L Denver flotation cell, 500 ml of tap water (Stenungsund municipal water with hardness 4° dH) was added and the mixing started. Then 5 minutes conditioning with 25 ml of a 1% (w/w) aqueous starch solution was performed, the collector was added as a 1% (w/w) solution, and conditioning was continued for 2.5 minutes. After the conditioning steps tap water was added so that a total volume of 1.4 L was obtained, the pH of the flotation mixture was adjusted to 9.5 with a 10% NaOH aqueous solution and the flotation was started. The experiment was performed at RT (20±1° C.). The rougher flotation, followed by two cleaning steps, was performed. All fractions (tailings, middlings and concentrate) were collected and analysed. Below there is a scheme illustrating the flotation steps performed and the different fractions collected.

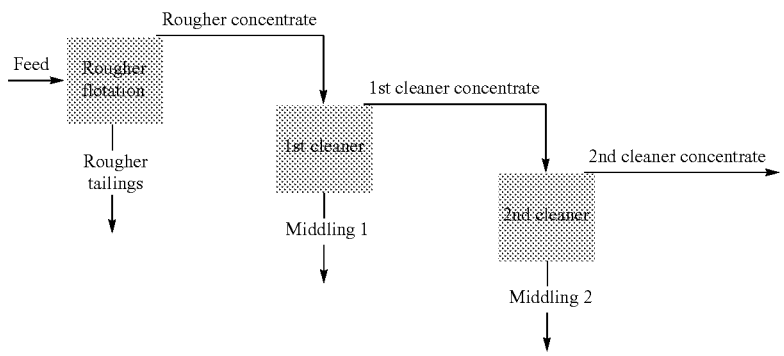

The collectors displayed in Table 1 were used in the flotation procedure above, and the flotation results with these collectors are displayed in Table 2.

TABLE 1

| Component | Collector 1 (Comparison) | Collector 2 (Comparison) | Collector 3 (Comparison) | Collector 4 |
|---|---|---|---|---|
| Tall oil fatty acid | 56 mol % | 30.2 mol % | 42 mol % | 57 mol % |
| N-acyl glycine[1] | 44 mol % | 0 mol % | 33 mol % | 36 mol % |
| Lactic acid ester of N-acyl glycine[1] | 0 mol % | 0 mol % | 0 mol % | 6 mol % |
| Lactic acid ester of Tall Oil Fatty Acid | 0 mol % | 69.8 mol % | 0 mol % | 0 mol % |
| Lactic acid | 0 mol % | 0 mol % | 25 mol % | 0 mol % |

[1] Acyl group derived from tall oil fatty acid
The percentages were calculated based on the total amount of moles of the different components in the respective compositions.

Collector 3 is a mixture of collector 1 and lactic acid. Collector 4 is a reaction product obtained by heating collector 3 at 100-120° C. for 1.5 hours at atmospheric pressure and then at 120-150° C. for 1 hour at a pressure of 13 mbar.

TABLE 2

| Collector | Fraction | Recovery $P_2O_5$ (%) | Grade of (%) | | | |
|---|---|---|---|---|---|---|
| | | | $P_2O_5$ | Fe | MgO | $SiO_2$ |
| 1 | Rougher concentrate | 88.8 | 26.2 | 8.22 | 2.41 | 10.2 |
| 1 | 1st cleaner concentrate | 82.7 | 30.63 | 5.52 | 1.36 | 6.43 |
| 1 | 2nd cleaner concentrate | 75.1 | 33.4 | 3.8 | 0.88 | 4.4 |
| 2 | Rougher concentrate | 84.1 | 27.6 | 7.8 | 8.7 | 2.2 |
| 2 | 1st cleaner concentrate | 76.7 | 32.57 | 4.59 | 1.07 | 4.78 |
| 2 | 2nd cleaner concentrate | 70.3 | 34.8 | 3.1 | 0.72 | 3.3 |
| 3 | Rougher concentrate | 88.9 | 26.9 | 7.7 | 2.27 | 9.9 |
| 3 | 1st cleaner concentrate | 82.5 | 31.38 | 5.01 | 1.25 | 6.08 |
| 3 | 2nd cleaner concentrate | 73.8 | 34.1 | 3.4 | 0.8 | 4.0 |
| 4 | Rougher concentrate | 89.1 | 26.5 | 7.94 | 2.35 | 9.9 |
| 4 | 1st cleaner concentrate | 83.8 | 31.0 | 5.21 | 1.29 | 6.13 |
| 4 | 2nd cleaner concentrate | 78 | 33.4 | 3.7 | 0.88 | 4.3 |

The values in Table 2 are weight percentages.

The results in Table 2 show that compared to using the N-acyl glycine (in Collector 1) there is an improvement in the recovery of $P_2O_5$ using the product of the invention (in Collector 4), and the grade of the product is at about the same level for both collectors. Compared to using the lactic acid ester of tall oil fatty acid (in collector 2) there is an even larger improvement in the recovery of $P_2O_5$ using the product of the invention (in Collector 4).

The invention claimed is:

1. A compound obtainable by reacting an N-acyl neutral amino acid or a salt thereof, or an N-acyl neutral amino acid oligopeptide or a salt thereof with a monohydroxy monocarboxylic acid or a salt thereof, wherein the N-acyl group is a group R—(C=O)— where R is a hydrocarbyl group having from 7 to 23 carbon atoms, optionally substituted.

2. A compound according to claim 1, where the neutral amino acid is selected from the group consisting of glycine, alanine, sarcosine, valine, leucine and isoleucine.

3. A compound according to claim 1, where the monohydroxy monocarboxylic acid is selected from the group consisting of lactic acid and glycolic acid.

4. A compound according to claim 1 having the structural formula

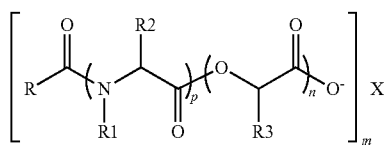

where R is a hydrocarbyl group having from 7 to 23 carbon atoms, optionally substituted; $R_1$ is H or $CH_3$; $R_2$ is H or a C1-C4 alkyl group; $R_3$ is H or $CH_3$; n is a number 1-20; p is a number 1-3; X is $H^+$ or a cation which is organic or inorganic, and m represents the valency of the cation and is a number 1-2.

5. A composition comprising:
a) a compound according to claim 1,
b) an N-acyl neutral amino acid or a salt thereof, and
c) a fatty acid RCOOH, where R is a hydrocarbyl group having from 7 to 23 carbon atoms, optionally substituted, or a salt thereof.

6. A composition according to claim 5 wherein a) is present in an amount of 1-20 mol %, b) is present in an amount of 30-60 mol % and c) is present in an amount of 40-60 mol %, wherein the amounts are calculated based on the total molar amount of a), b) and c).

7. A method for froth flotation of non-sulfidic ores, the method comprising:
a) conditioning a pulped phosphate ore, wherein the phosphate ore comprises a calcium phosphate mineral or a mixture of such minerals, and gangue minerals, with an effective amount of a calcium phosphate mineral collector reagent, which is a compound as defined in claim 1, and optionally other flotation aids and
b) performing a froth flotation process to recover the calcium phosphate mineral(s).

8. A pulp comprising phosphate ore, a compound according to claim 1, and optionally a depressant.

9. A compound obtainable by reacting an N-acyl neutral amino acid or a salt thereof, or an N-acyl neutral amino acid oligopeptide or a salt thereof with a monohydroxy monocarboxylic acid or a salt thereof, wherein the compound has the structural formula

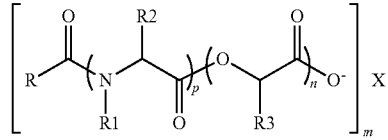

where R is a hydrocarbyl group having from 7 to 23 carbon atoms, optionally substituted; $R_1$ is H or $CH_3$; $R_2$ is H or a C1-C4 alkyl group; $R_3$ is H or $CH_3$; n is a number 1-20; p is a number 1-3; X is $H^+$ or a cation which is organic or inorganic, and m represents the valency of the cation and is a number 1-2.

10. A compound according to claim 9, where the neutral amino acid is selected from the group consisting of glycine, alanine, sarcosine, valine, leucine and isoleucine.

11. A compound according to claim 9, where the monohydroxy monocarboxylic acid is selected from the group consisting of lactic acid and glycolic acid.

12. A composition comprising:
a) a compound according to claim 9,
b) an N-acyl neutral amino acid or a salt thereof, and
c) a fatty acid RCOOH, where R is a hydrocarbyl group having from 7 to 23 carbon atoms, optionally substituted, or a salt thereof.

13. A composition according to claim 12 wherein a) is present in an amount of 1-20 mol %, b) is present in an amount of 30-60 mol % and c) is present in an amount of 40-60 mol %, wherein the amounts are calculated based on the total molar amount of a), b) and c).

14. A method for froth flotation of non-sulfidic ores, the method comprising:
a) conditioning a pulped phosphate ore, wherein the phosphate ore comprises a calcium phosphate mineral or a mixture of such minerals, and gangue minerals, with an effective amount of a calcium phosphate mineral collector reagent, which is a compound as defined in claim 9, and optionally other flotation aids and
b) performing a froth flotation process to recover the calcium phosphate mineral(s).

\* \* \* \* \*